Figure 1:
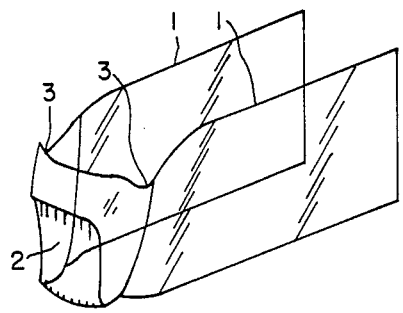

United States Patent
von Weissenfluh et al.

[11] Patent Number: 4,718,849
[45] Date of Patent: Jan. 12, 1988

[54] SHEET-LIKE DENTAL DIE

[76] Inventors: Hans von Weissenfluh, CH-6573 Magadino; Giacomo Richner, Via Lucino 20, CH-6932 Breganzona, both of Switzerland

[21] Appl. No.: 836,960
[22] Filed: Mar. 6, 1986
[51] Int. Cl.[4] .............................................. A61C 5/04
[52] U.S. Cl. ...................................... 433/39; 433/229
[58] Field of Search .................... 433/229, 39, 40, 214

[56] References Cited

U.S. PATENT DOCUMENTS

| | | | |
|---|---|---|---|
| 2,594,367 | 4/1952 | Tofflemire | 433/39 |
| 4,129,946 | 12/1978 | Kennedy | 433/37 |
| 4,449,928 | 5/1984 | Weissenfluh | 433/229 |
| 4,608,021 | 8/1986 | Barrett | 433/229 |

Primary Examiner—Robert Peshock
Attorney, Agent, or Firm—David M. Ostfeld

[57] ABSTRACT

The sheet-like dental die, with the anatomical characteristics of the profile of a certain type of tooth, made of a material permeable to light and to UV rays and which does not bind to hardenable filling synthetic materials by radiation, is deposited according to the configuration and utilization about the tooth to be filled from the tongue or vestibule side and the two even lobes (1) are pressed against each other on the opposite side by means of a dentist pincer while the filling is irradiated to allow its polymerization or at least its introduction.

5 Claims, 4 Drawing Figures

SHEET-LIKE DENTAL DIE

The present invention refers to a die for the external shaping of dental stoppings of oral, coronal, and proximal situation, hence of the whole coronal region.

In case dental stoppings, consisting of amalgams or self-hardening cements on an organic or an organic basis, are placed the external shaping is performed in known manner with the known dental tools partly before partly after hardening of the stopping material. In recent times more and more filling materials consisting of single-component synthetics are applied which for polymerisation—or at least for starting it—need light or UV radiation. It is characteristic for these synthetics that their polymerisation turns out incomplete in the presence of oxygen, hence monomerous, partially oxidized base material is present instead of the desired polymeride. Such oxidized monomerous base material is to be removed from the surface of the stopping because it exhibits totally insufficient mechanical properties.

In order to avoid the contact with the surrounding air during polymerisation, various masking devices have been proposed. One such device has been known through the Swiss Pat. No. 626,247; however this is suitable only for vestibular stoppings, because during polymerisation it is pressed onto the tooth from the outside.

Furthermore it is state of the art to bend an initially flat, U-shaped strip of synthetic, UV-transparent material around the tooth to be filled and to press its end together on the vestibular side with a suitable instrument during the time the stopping is irradiated with an UV lamp.

This procedure has the disadvantage that only such external shapes of stoppings are possible which have a basically flat development. Hence such a stopping has to be built up in several steps or one must eventually remove large amounts of surplus material, a procedure which is tedious and time consuming, which is very difficult in the space between the teeth. Also elastic foils have been proposed; they have the disadvantage to squeeze the filling material out of the cavity just filled in case the foil is applied as tightly as required for the desired result.

The problem to be solved with the present invention is the creation of a sheet-like dental die for the shaping of dental stoppings in the whole coronal region, whereby the material of the die is to be transparent for light and UV rays, and may not adhere to the radiation curing single component synthetics suitable for filling purposes. This said die shall be shaped in such manner that for one single type of tooth—an upper incisor or a lower canine tooth e.g.—two dies shall suffice: One for fillings in the lingual and proximal range, another one for fillings in the vestibular and proximal range; this said die furthermore shall allow for adjusting to the different sizes of one single type of tooth by the remaining and limited strain of its material. It is a further goal of this invention to allow the handling of this said die without additional and complex tools.

The solution of this problem according to this invention is characterized in that the die, essentially U-shaped, bears in its middle portion the typical anatomical features of the tooth to be treated and takes account of the contours of the gums, in that the thickness of the material of the die in the range of the proximal flanks of he tooth is reduced in order to allow for a small number of sizes or even one single size die for one special tooth in all its variations in size and shape.

By means of the accompanying drawings the invention shall be explained in detail.

Figure 2:
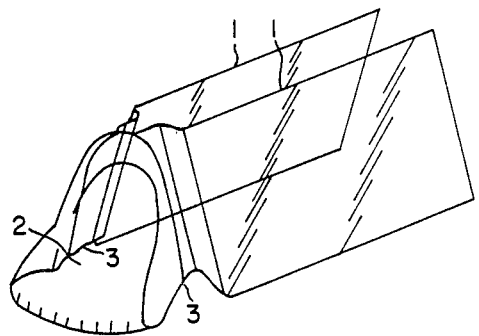

They show:

FIG. 1. a dental die according to this invention in the embodiment for an upper incisor FIG. 2 a dental die according to this invention in the embodiment for a lower canine tooth.

Figure 3:
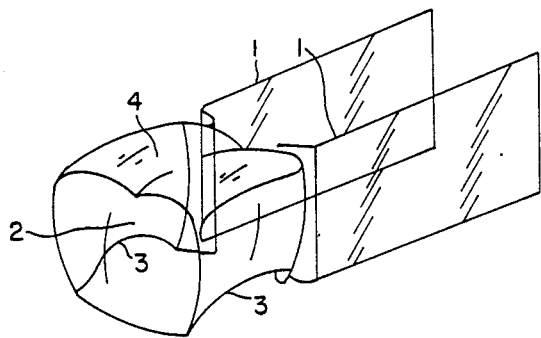

FIG. 3 a dental die according to this invention in the embodiment for a lower molar tooth.

Figure 4:
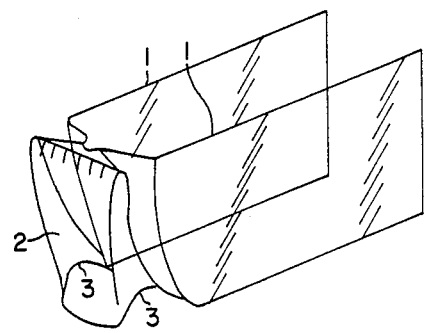

FIG. 4 a dental die according to this invention in the embodiment for a lower incisor for a frontal filling.

The dental die according to this invention in the embodiment of FIG. 1 is consisting of two flat fins 1 and a shaped middle portion 2 bearing the essential features of the palatinal side and the incision edge of an upper incisor. Furthermore the middle portion 2 is shaped in such manner as to fit the upper incisor snugly at its lateral region in order to take care of proximal fillings.

The two flat fins 1 each carray an indentation 3 leaving room for the interdental gums. The thickness of the material in the region of the lateral flanks of the tooth is reduced to allow for the use of one sinle die for all the different sizes and shapes of upper incisors. During application of the die the two flat fins 1 are grasped with dental tweezers so close to the tooth that the die fits the tooth tightly when the flat fins 1 are pressed together.

A further embodiment not shown in a drawing has essentially the same structure with the exception that in the middle portion 2 it is bearing the features of the lower incisor. The embodiment according to FIG. 2 is for a lower canine tooth. It is, as the one according to FIG. 1, articulated into two flat fins 1 and a middle portion 2, whereby the flat fins 1 are inclined with respect to each other. The middle portion 2 is, according to its purpose shaped such as to fit a lower canine tooth in case it is put onto such tooth from the lingual side nd tightened by pulling together flat fins 1. Also this embodiment has two indentations 3 leaving room for the interdental gums. In the region of the lateral flanks of the tooth the material of the die is as thin as to enable one size die to take care of essentially all sizes and shapes of lower canine teeth.

FIG. 3 shows the embodiment of a lower molar tooth. The structural elements of the embodiments according to FIGS. 1 and 2 here are present as well: The two flat fins 1, the middle portion 2 and the two indentations 3. The difference between this embodiment and the two former ones is that the die is also shaped to take care of the chewing area; hence it also has a top surface 4. The wealth of shapes and individual features of molar teeth is so big and manifold, that the top surface 4 is only exhibiting the generally typical features. Thus it is taken into account that the stopping has to be worked over in the range of the chewing area which, however, is general practise also with other types of fillings, be they of organic or anorganic nature. The reduced thickness of the die in the range of the lateral flanks of the tooth enables the dentist—irrespective of the increased stiffness of the die in the middle portion 2—to manage with only a limited number of sizes of dies, because such a die retains a limited malleability.

The embodiment according to FIG. 4 is suitable for fillings on the frontal side of a lower incisor. The novel and inventive features also here are the two flat fins 1 adjacent to the molded middle portion 2 whereby two indentations 3 mark the transition between them in order to take care of the shape of the interdental gums. The die according to FIG. 4 is put by the dentist onto the tooth from the vestibular side and pressed together at the two flat fins 1 by means of a suitable instrument on the lingual side.

We claim:

1. Sheet-like dental die made from light- and UV-transparent material not adhering to radiation-curing single-component synthetics for the external shaping of fillings in the whole coronal region of teeth, comprising:

an essentially preshaped U-shaped foil having a middle portion (2) shaped to the typical anatomical features of substantially the entire tooth to be filled, and having two flat fins (1), one at each side of and connected to said middle portion (2), said fins (1) adapted to be grasped and squeezed to tighten said foil by means of a suitable instrument.

2. Sheet-like dental die according to claim 1 characterized in that in region of the transition from the middle portion (2) to the two flat fins (1) it has two indentations (3) to take care of the shape of the gums.

3. Sheet-like dental die according to claims 1 or 2 characterized by a reduced thickness of the material in the region of the lateral flanks of the tooth.

4. Sheet-like dental die according to claims 1 or 2 characterized by having the anatomical features of the tooth to be filled, in the lingual and proximal region.

5. Sheet-like dental die according to claims 1 or 2 characterized by having the anatomical features of the tooth to be filled, in the vestibular and proximal region.

* * * * *